Figure 1:
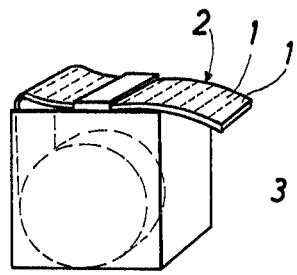

U.S. Patent  Sep. 18, 1979  4,167,832

United States Patent [19]

Zetterquist et al.

[11] 4,167,832
[45] Sep. 18, 1979

[54] MEANS OF PRESERVING CUT FLOWERS PLACED IN WATER

[76] Inventors: Lars G. Zetterquist, Skånevägen 10, S-22228 Lund, Sweden; Poul H. Ahm, Bregnerødvej 170, DK-3460 Birkerød; Ole Rosdahl, Vaengestien 5, DK-2840 Holte, both of Denmark

[21] Appl. No.: 849,654

[22] Filed: Nov. 8, 1977

[30] Foreign Application Priority Data

Jul. 4, 1977 [GB] United Kingdom ............... 27946/77

[51] Int. Cl.$^2$ ..................... A01G 5/06; A01N 3/02
[52] U.S. Cl. ......................... 47/1 R; 47/58; 47/55; 47/7; 47/DIG. 2; 71/68
[58] Field of Search .................. 47/7, DIG. 2, 84, 58, 47/55, 1; 71/68

[56] References Cited

U.S. PATENT DOCUMENTS

| | | |
|---|---|---|
| 1,824,674 | 9/1931 | L'Hommedieu ..................... 47/7 |
| 1,860,255 | 5/1932 | L'Hommedieu ..................... 47/7 |
| 2,317,631 | 4/1943 | Meyer ............................ 47/DIG. 2 |
| 2,923,094 | 2/1960 | Ryan ................................. 47/58 |
| 3,134,661 | 5/1964 | Sheppard ...................... 47/DIG. 2 |
| 3,321,865 | 5/1967 | Routon ............................. 47/55 |

FOREIGN PATENT DOCUMENTS

| | | |
|---|---|---|
| 1482291 | 5/1969 | Fed. Rep. of Germany ...... 47/DIG. 2 |
| 2518446 | 12/1975 | Fed. Rep. of Germany ............. 71/68 |
| 2256717 | 8/1975 | France ........................................ 71/68 |

*Primary Examiner*—Robert E. Bagwill
*Attorney, Agent, or Firm*—Cushman, Darby & Cushman

[57] ABSTRACT

A means of preserving cut flowers placed in water, said means comprising one or more bactericidal substances, with the possible additions of one or more bacteriostatic substances, one or more surfactants, and/or one or more nutritious substances. The bactericidal substance may be 1.3-dichloro-5.5-dimethylhydantoin which splits off chlorine in relation to the pH-value of the aqueous solution. Said derivative forms part of a thin coating applied to the front surface of a strip of paper or cardboard which is very small in relation to the length of the stems of the flowers. A layer of non- (or very little) water-soluble self-adhesive substance is applied to the back surface of the strip, the substance being tolerable by the stems of flowers. The consumer can easily fasten the strip unit close to the lower end of the stem before placing the latter in water. The strip unit is easily dispensible from a protective container.

15 Claims, 4 Drawing Figures

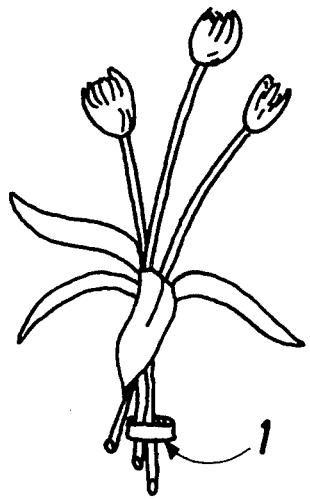

MEANS OF PRESERVING CUT FLOWERS PLACED IN WATER

The invention relates to a means of preserving cut flowers placed in water, said means comprising one or more bactericidal substances, with the possible additions of one or more bacteriostatic substances, one or more surfactants, for example the chemical marketed under the name "Tween" 20 "(tris (polyoxyethylene) sorbitan monolaurate)", and/or one or more nutritious substances.

Preserving cut flowers placed in water by adding certain substances to the water is known. Such substances may, for example, increase the osmotic pressure in the cells of the epidermis of the leaves in such a way that the stomata in the epidermis are closed to a certain degree, thereby reducing the vaporization from the leaves and increasing the turgor in the leaves and flowers. Cane sugar is a substance of the kind mentioned above, another kind being the surfactants which prevent the formation of mucus on the cut of the stem and the bactericidal substances which prevent infection from developing in the cut.

It is problematic, however, finding suitable bactericidal substances which are non-poisonous for humans, yet very effective and which are so easy to administer that a customer buying a bouquet of flowers at a florist's need not add a preserving means to the water in which the stems of the flowers are to be immersed. It is the aim of the present invention to disclose a preserving means of the kind mentioned above which will solve the aforementioned problem.

The preserving means according to the invention is characterized in that the bactericidal substance is a compound which splits off chlorine in relation to the pH-value of the aqueous solution, the splitting off of the chlorine rising as the pH-value falls, preferably 1.3-dichloro-5.5-dimethylhydantoin, said compound forming part of a thin coating applied to the front surface of a strip of paper or cardboared which is very small in relation to the length of the stems of the flowers, said strip of paper or cardboard preferably being non-absorptive, a layer of non- (or very little) water-soluble self-adhesive substance being applied to the back surface, said substance being tolerable by wet as well as dry stems of flowers even during prolonged contact herewith, so that the consumer can easily fasten the strip unit close to the lower end of the stem before placing said stem in water, whereby the strip unit can be cut or formed in such a way as to make the unused strip unit easily dispensable from a protective container. By using this preserving means, the bacteria in the water are killed effectively. No more chlorine than is necessary is given off. By providing the strip in question with a self-adhesive substance of the kind mentioned above, a florist can when selling a bouquet easily fasten said strip unit close to the lower end of one or more stems and when the customer later immerses the stems in water, he or she will not need to add a preservative. Upon immersion of the stems of the bouquet in the water, the bactericidal substance is released, usually over a period of several days. 1.3-dichloro-5.5-dimethylhydantoin has been proven non-poisonous for humans and especially effective in water.

According to the invention, the amount of hydantoin derivative in the coating may range from 1.5 to 10 $mg/cm^2$, preferably from 2 to 8 $mg/cm^2$, better yet from 2 to 3.9 $mg/cm^2$, the most preferred being 3.8 $mg/cm^2$. A very reliable supply of hydantoin derivative to the water is hereby achieved, as it is possible for said derivative, which is in dry form, to be given off gradually.

Furthermore according to the invention, the coating may contain a filler such as carboxymethyl cellulose, in which particles of hydantoin derivative are distributed, said filler functioning as a suspending substance for the hydantoin upon dissolution in the water.

Moreover according to the invention the amount of filler and hydantoin derivative per strip unit may be approximately 2 mg and approximately 23 mg respectively, said strip unit being intended for 0.5 l water. These amounts of filler and derivative have in practice been proven preferable.

According to the invention the coating may be applied as a liquid which besides the filler and hydantoin derivative contains approximately 78 mg of water per strip.

According to the invention the strip may be artificially dried, preferably by passage through a hot stream of air, thus ensuring that the hydantoin derivative is effectively applied to the strip.

Furthermore according to the invention the liquid may be applied to the strip by means of rolling and preferably dried by contact with hot metal surfaces, thereby achieving an even distribution of the liquid.

It is particularly preferred that the adhesive is of the kind marketed under the name "Beiersdorff B 4".

Furthermore according to the invention in the strip unit together with many unused strip units of the same kind may form an easily rolled ribbon, kept in an easily transportable container from which ribbon the strip units may be torn off separately. This ribbon facilitates removal when the florist needs a strip unit for a bouquet.

Moreover according to the invention the strip unit together with many strip units of the same kind may be kept on a preferably rolled carrier ribbon, said strip units being adhered hereto, but easily removable herefrom. Thus extra protection of the surface of the strip unit facing the ribbon is achieved.

It is particularly preferred that the individual strip unit weighs 50–160 $g/m^2$ and is made of wood-free cardboard.

Finally, according to the invention the strip unit may be shaped as a very oblong rectangle, preferably having the dimensions 12 mm×50 mm. This dimension has proven practical, as the strip unit is large enough to carry sufficient amounts of the desired substances, yet is small enough to go unnoticed by the customer who has bought the bouquet.

Figure 2:
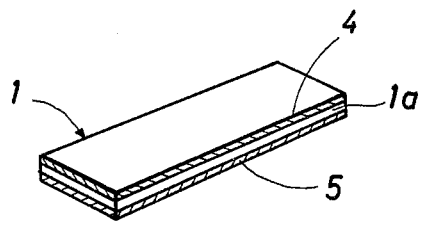
Figure 3:
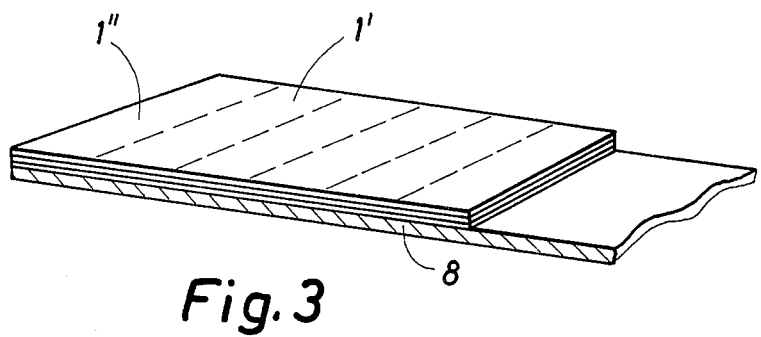

The present invention will be described below with reference to the accompanying drawings in which FIG. 1 is a perspective view of a container with a rolled ribbon made up of many adjacent strip units according to the invention, from which container the strip units may be removed separately, FIG. 2 is a strip unit according to the invention before being fastened at the lower end of a stem in the bouquet, FIG. 3 is a perspective view of many adjacent strip units placed on a common carrier ribbon.

Figure 4:
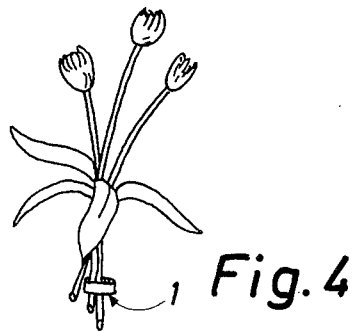

FIG. 4 is a perspective view of a bouquet of flowers on which a strip unit according to the invention has been mounted.

The container 3 shown in FIG. 1 contains a rollable ribbon 2, which is divided into a number of connected strip units 1. The strip units, which are made of paper or cardboard (preferably non-absorptive) may be easily torn off. Incidentally, the container is preferably made of cardboard and is relatively small so as to be easily transportable.

In FIG. 2 a preserving means according to the invention is seen in the shape of a rectangular strip unit 1a, whose front surface is provided with a coating 4 containing at least a bactericidal compound, which splits off chlorine in relation to the pH-value of the water in which the preserving means is later immersed in connection with a bouquet. However, the splitting off of the chlorine rises as the pH-value falls. The compound mentioned is preferably 1.3-dichloro-5.5-dimethylhydantoin. A layer 5 of non- (or very little) water-soluble self-adhesive substance is applied to the back surface of the strip 1a, the quality of said adhesive substance being tolerable by wet as well as dry stems of flowers even during prolonged contact herewith. The preserving means, which is indicated in its entirety by 1, may have a rectangular shape as shown, but it may also have another shape, e.g. triangular or oval.

In order to use the preserving means 1 (after having removed it from the ribbon 2), it is fastened to the lower end of one or more stems in a bouquet as shown in FIG. 4. As seen, the portions of self-adhesive substance at each end of layer 5 will be made to contact each other. As the preserving means 1 in FIG. 4 is rather small in relation to the length of the stems of the flowers, a customer buying a bouquet will hardly notice the strip unit which the florist has attached to the bouquet.

The amount of hydantoin derivative, which is part of the coating, may range from 1.5 to 10 $mg/cm^2$, preferably from 2 to 8 $mg/cm^2$, better yet from 2 to 3.9 $mg/cm^2$, the most preferred amount being 3.8 $mg/cm^2$. Besides bacteriostatic substances, surfactants and nutritious substances, if any, the coating may contain a filler, such as carboxymethyl cellulose. Particles of the hydantoin derivative are evenly distributed in the filler. When the preserving means is immersed in water by immersing the stems of the bouquet, the carboxymethyl cellulose will act as a suspending substance for the hydantoin derivative, which is dissolved in such a way that the latter does not collect at the bottom of the vase when the water is allowed to stand for a long period of time.

It is particularly preferred that the amount of carboxymethyl cellulose and the hydantoin derivative per strip be approximately 2 mg and approximately 23 mg respectively, on the assumption that the strip unit is intended for 0.5 l water.

The adhesive in layer 5 may be a non-water-soluble self-adhesive substance, for example, the kind marketed under the name "Beiersdorff B4". "Biersdorff B4 is a rubber based adhesive". It is essential that the adhesive has no effect upon the bactericidal or the bacteriostatic compound in the coating 4. The strip 1a is preferably non-absorptive so that contact between layers 4 and 5 may be avoided.

The strip units 1', as shown in FIG. 3, may be placed on a common carrier ribbon 8 which may, for example, be made of silicone paper. Layer 5 faces the carrier ribbon 8. The individual strip unit may be easily removed from the adjacent strip unit and/or the carrier ribbon.

According to the invention the preserving means may be made most easily out of large sheets of paper or cardboard preferably weighing 50–160 $g/m^2$. Especially wood-free cardboard is well suited. This material is coated with an aqueous liquid, containing 2 mg carboxymethyl cellulose, 23 mg hydantoin derivative and 78 mg water per strip, by conveying the cardboard, for example at an even pace past a vat, in the bottom of which is a slot, said vat being filled with the solution mentioned. The layer of adhesive 5 is applied before the coating 4. The cardboard is then quickly conveyed through a drier, for example one which operates with a hot air stream.

Instead of following the method described above, the coating 4 may be rolled on. In order to remove the water, the cardboard must be conveyed during the last part of the operation over hot metal surfaces to evaporate the water.

The strip unit shown in FIG. 2 is preferably 12 mm × 50 mm.

EXAMPLE 1

A bouquet of tulips was placed in a vase of water containing 0.5 l tap water (pH 6.8). On the sixth day after immersion, the heads of the flowers began to hang and on the seventh day, the leaves hung as well. On the eighth day the bouquet was wilted. The bacterial growth in the water had risen from the first day.

A similar bouquet was provided with the strip unit according to the invention and placed in 0.5 l tap water (pH 6.8). Not until the eleventh day were the flowers wilted. The bacterial growth was not appreciable until the ninth day.

EXAMPLE 2

A bouquet of five chrysanthemums and five roses were placed in a vase containing 0.5 l tap water (pH 6.8). On the third day after immersion the leaves began to hang and on the sixth day the heads of the flowers hung as well. On the eighth day the bouquet was wilted. The bacterial growth had risen steadily from the first day.

A similar bouquet which was provided with the strip unit according to the invention and placed in 0.5 l tap water (pH 6.8) showed increased durability, staying fresh until the 11th day. The bacterial growth did not start until the eighth day.

EXAMPLE 3

A bouquet of seven Gerbera and seven daisies were placed in a vase containing 0.5 l tap water (pH 6.8). The leaves began to sag on the third day and the flowers on the fourth day. On the fifth day the bouquet was wilted. The bacterial growth had risen steadily from the first day.

A similar bouquet which was provided with the strip unit according to the invention and placed in 0.5 l tap water (pH 6.8) showed increased durability, showing no signs of wilting until the 13th day. There was no appreciable bacterial growth until the 12th day.

The strip unit mentioned in the examples were provided with 1.3-dichloro-5.5-dimethylhydantoin, by being coated with a liquid comprising hydantoin derivative, carboxymethyl cellulose and water, said water being removed by slightly heating the strip unit. The hydantoin derivative was readily soluble in the water.

We claim:
1. A means suitable for preserving cut flowers in water, said means comprising a support strip, a bacteriostatic substance which splits off chlorine at an increas- ing rate as the pH value falls as a thin coating on the front surface of the strip and a self-adhesive having at most slight solubility in water on the back surface of the strip, said strip being relatively small compared to the length of stems of the flowers.

2. Flowers having attached around the stems thereof the preserving means of claim 1.

3. A preserving means according to claim 1 wherein the strip is made of a material selected from the group consisting of paper and cardboard.

4. A preserving means according to claim 1 wherein the bacteriostatic substance is 1,3-dichloro-5,5-dimethylhydantoin.

5. A preserving means according to claim 4 wherein the amount of the 1,3-dichloro-5,5-dimethylhydantoin is 1.5 to 10 mg/cm$^2$.

6. A preserving means according to claim 5 wherein the amount of the 1,3-dichloro-5,5-dimethylhydantoin is 2 to 8 mg/cm$^2$.

7. A preserving means according to claim 6 wherein the amount of the 1,3-dichloro-5,5-dimethylhydantoin is 2 to 3.9 mg/cm$^2$.

8. A preserving means according to claim 7 wherein the amount of the 1,3-dichloro-5,5-dimethylhydantoin is 3.8 mg/cm$^2$.

9. A preserving means according to claim 4 containing the 1,3-dichloro-5,5-dimethylhydantoin distributed as particles in carboxymethyl cellulose.

10. A preserving means according to claim 9 wherein per strip there are present approximately 2 mg of 1,3-dichloro-5,5-dimethylhydantoin and 23 mg of carboxymethyl cellulose.

11. Flowers having attached around the stems thereof the preserving means of claim 4.

12. Flowers according to claim 11 wherein the strip of the preserving means is made of a material selected from the group consisting of paper and cardboard.

13. A preserving means according to claim 1 wherein the strip is the shape of a rectangle having the dimensions 12 mm×50 mm.

14. A ribbon having applied thereto a plurality of said strips of claim 1 in a form adapted to be individually removed from said ribbon.

15. A combination of a dispensing container and a rolled ribbon according to claim 14.

* * * * *